(12) United States Patent
Adleff et al.

(10) Patent No.: US 8,322,993 B2
(45) Date of Patent: Dec. 4, 2012

(54) OSMOTIC PUMP COMPRISING A PRESSURE DEVICE FOR PRESSURIZING THE SOLVENT

(75) Inventors: Helge Adleff, Berlin (DE); Thilo Philipp Guschauski, Berlin (DE)

(73) Assignee: Acuros GmbH, Berlin (DE)

( * ) Notice: Subject to any disclaimer, the term of this patent is extended or adjusted under 35 U.S.C. 154(b) by 944 days.

(21) Appl. No.: 12/268,325

(22) Filed: Nov. 10, 2008

(65) Prior Publication Data

US 2009/0129945 A1   May 21, 2009

(30) Foreign Application Priority Data

Nov. 13, 2007   (EP) ..................... 07022030

(51) Int. Cl.
*C25B 9/08* (2006.01)
*F04F 99/00* (2009.01)
*H02K 44/02* (2006.01)
(52) U.S. Cl. .............. 417/53; 417/48; 204/600
(58) Field of Classification Search .......... 417/48, 417/53; 204/600
See application file for complete search history.

(56) References Cited

U.S. PATENT DOCUMENTS

| | | |
|---|---|---|
| 3,604,417 A | 9/1971 | Stolzenberg et al. |
| 4,193,398 A | 3/1980 | Refson |
| 4,505,702 A | 3/1985 | Peery et al. |
| 4,619,652 A | 10/1986 | Eckenhoff et al. |
| 5,672,167 A | 9/1997 | Athayde et al. |
| 7,419,484 B2 | 9/2008 | Schiltges et al. |
| 2005/0034842 A1* | 2/2005 | Huber et al. ............... 165/80.4 |
| 2005/0131389 A1* | 6/2005 | Peterson et al. .......... 604/892.1 |
| 2006/0116664 A1* | 6/2006 | Richter et al. ............ 604/892.1 |
| 2008/0152694 A1* | 6/2008 | Lobl et al. .................. 424/427 |

FOREIGN PATENT DOCUMENTS

| | | |
|---|---|---|
| WO | WO 94/05354 A1 | 3/1994 |
| WO | WO 2004/062714 A1 | 7/2004 |
| WO | WO 2005/107835 A1 | 11/2005 |

OTHER PUBLICATIONS

Theeuwes, Yum: Principles of the Design and Operation of Generic Osmotic Pumps for the Delivery of Semisolid or Liquid Drug Formulations.
Annals of Biomedical Engineering, vol. 4, No. 4, Dec. 1976, p. 343-353. Academic Press Inc.

* cited by examiner

*Primary Examiner* — Tracie Y Green

(57) ABSTRACT

An osmotic pump comprises a first chamber (8) comprising an osmotically active substance (18), a second chamber (15) arranged to be filled with a solvent (17), and a semi-permeable barrier (14) separating the first chamber (8) from the second chamber (15). The semi-permeable barrier (14) is impermeable to the osmotic active substance and permeable to the solvent (17). The osmotic pump further comprises a pressure device (60) in fluid communication with the second chamber (15), wherein the pressure device (60) is arranged for pressurizing the solvent in the second chamber.

17 Claims, 7 Drawing Sheets

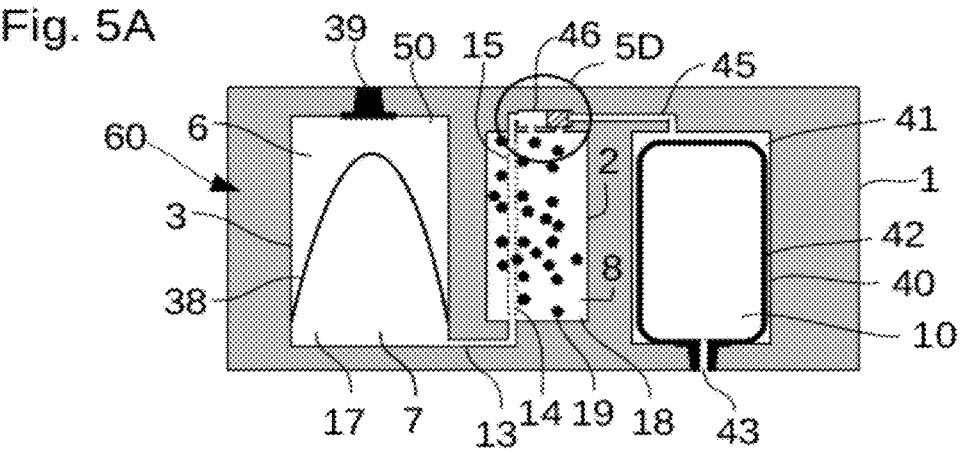
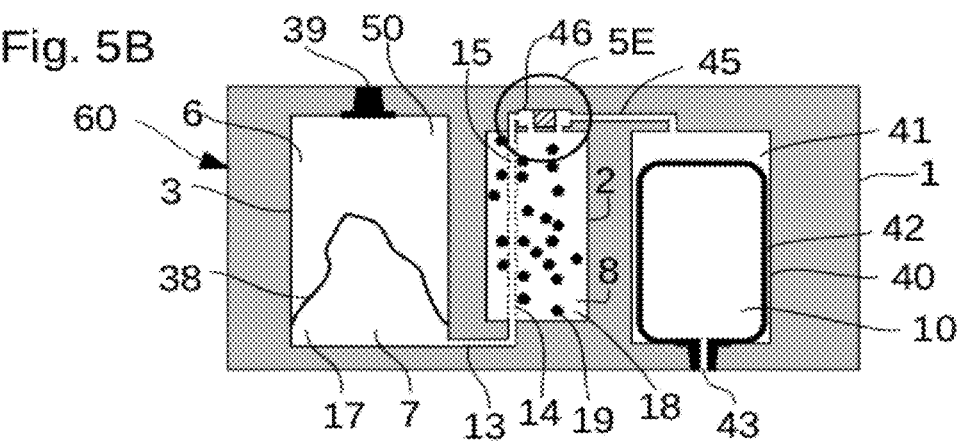
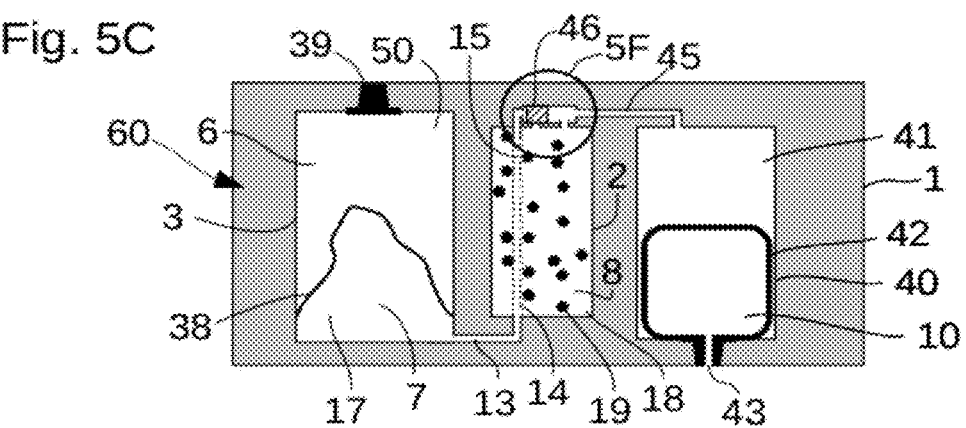

OSMOTIC PUMP COMPRISING A PRESSURE DEVICE FOR PRESSURIZING THE SOLVENT

This specification describes embodiments relating to an osmotic pump for delivering fluids at low flow rates for prolonged periods of time. In particular, it relates to an osmotic pump comprising a pressurized reservoir of the solvent that is imbibed by the osmotic pump through the pores of at least one semi-permeable membrane.

BACKGROUND OF THE INVENTION

In the last decades much effort has been made in development of micropumps due to an increasing demand in different microfluidic applications like microanalytics, micro reaction technology, lab-on-a-chip applications, point-of-care diagnostics and drug-delivery devices. Other fields of interest include, but are not limited to, micro-dispensing of lubricants, fragrances, perfumes, scents, adhesives, nutrients, fertilizers and the like. Controlled release of beneficial agents over a prolonged period of time is one field of special interest.

Osmotic micropumps are designed to control displacement of fluids over prolonged periods of time and are therefore appropriate for many applications. A typical arrangement of an osmotic pump comprises at least one compartment containing an osmotic agent that is at least partially in direct contact with a semi-permeable membrane. The osmotic agent generates an osmotic potential and hence a pressure across the semi-permeable membrane and thereby imbibes solvent through the membrane. The solvent can be taken from another compartment or, e.g. in respect to implantable osmotic pumps, be imbibed from the surrounding media of the pump. The osmotic process generates a liquid phase by dissolution or dilution of the osmotic agent. The liquid phase can be used directly or be deployed as a driving fluid to displace a pumped fluid from another compartment. If necessary, the driving fluid and the pumped fluid can be separated by a piston, a flexible or elastic impermeable membrane or other movable means preventing contamination of the pumped fluid.

Osmotic pumps have many advantages over other micropumps such as low costs of manufacture, reliability, pressure capability and other aspects.

Commonly known osmotic pumps, however, can hardly be switched on and off instantly in an easy way or provide different flow rates between which one can easily switch. These aspects, however, are desired for many applications where e.g. a very low basal flow rate is desired with an additional initial or intermittently flushing at much higher flow rates. It is also often desired to have different basal flow rates available. In many drug delivery applications it is also desired, that a bolus dosage of the therapeutic substance can be delivered when needed in addition to the basal delivery rate.

Osmotic pumps are for instance described in WO 2005/107835 A1, U.S. Pat. No. 5,672,167, U.S. Pat. No. 4,505,702, U.S. Pat. No. 4,619,652 and the publication by Theeuwes and Yum, ANNALS OF BIOMEDICAL ENGINEERING, Vol. 4 No. 4, pp. 343-353, December 1976.

U.S. Pat. No. 3,604,417 describes an osmotic pump for long-term injection of a medicament. The osmotic pump includes a first part comprising a compartment filled with a concentrated solution. The compartment is delimited on one side by a moving piston and on another side by a membrane. The first part is inserted into a second part of the osmotic pump filled with a solvent to form a solvent chamber. The second part includes a moving piston to prevent formation of air pockets in the solvent chamber.

WO 2004/062714 A1 describes an automatic hydrogel-based extracorporal fluid conveyor. The fluid conveyor includes a swellable hydrogel.

WO 94/05354 A1 describes a fluid driven dispensing device with a piston driven by a fluid discharged from an osmotic engine.

An extracorporal osmotic pump is described in U.S. Pat. No. 4,193,398. The osmotic pump includes a first chamber containing an osmotic fluid and a second chamber containing water. A semipermeable membrane is arranged between the two chambers. The second chamber is formed by a polymeric bag.

SUMMARY OF THE INVENTION

According to an embodiment an osmotic pump is provided which comprises a first chamber comprising an osmotically active substance, a second chamber arranged to be filled with a solvent, and a semi-permeable barrier separating the first chamber from the second chamber. The semi-permeable barrier is impermeable to the osmotic active substance and permeable to the solvent. The osmotic pump further comprises a position-independent pressure device in fluid communication with the second chamber, wherein the pressure device is arranged for pressurizing the solvent in the second chamber.

The solvent is imbibed by the osmotic action of the osmotically active substance through the semi-permeable membrane into the first chamber in order to generate a driving fluid. The solvent is pressurized in the second chamber by the pressure device to enable the solvent to get substantially completely into contact with the semi-permeable barrier. This ensures that the semi-permeable barrier is completely wetted or covered by the solvent to maintain the osmotically driven flow of the solvent into the first chamber at its designated flow rate. Furthermore, the pressure device presses the solvent into the second chamber irrespective of the orientation, location or position of the osmotic pump which is of great importance for mobile applications. Particularly, the pressure device is arranged to pressurize the solvent independent from the relative position and orientation of the pressure device to the second chamber. Typically, the pressure device is arranged to pressurize substantially permanently the solvent during operation of the osmotic pump.

BRIEF DESCRIPTION OF THE DRAWINGS

A full and enabling disclosure of the present invention, including the best mode thereof, to one of ordinary skill in the art, is set forth more particularly in the remainder of the specification, including reference to the accompanying figures. Therein:

FIGS. 5A to 5F show yet a further embodiment of an osmotic pump at different phases of operation, wherein FIGS. 5D to 5F show enlarged views of a valve deployed to switch the osmotic pump.

DESCRIPTION OF THE PREFERRED EMBODIMENT

Figure 1A:
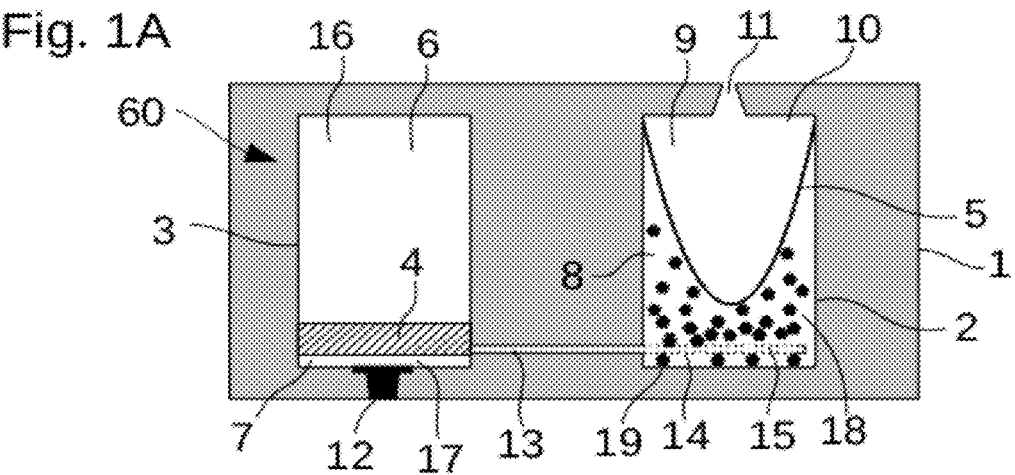
FIGS. 1A to 1C show an embodiment of an osmotic pump at different phases of operation.

It is to be understood that this invention is not limited to the particular structures, process steps, applications or materials disclosed herein, but is extended to equivalents thereof as would be recognized by those ordinarily skilled in the relevant arts. It should also be understood that terminology employed herein is used for the purpose of describing particular embodiments only and is not intended to be limiting. The invention will now be described in detail with reference to a few exemplary embodiments, as illustrated in accompanying drawings. In the following description, numerous specific details are set forth in order to provide a thorough understanding of the invention. However, it will be apparent to one skilled in the art that the invention may be practiced without some or all of these specific details.

It must be noted that, as used in this specification and the appended claims, the singular forms "a," "an," and "the" include plural referents unless the context clearly dictates otherwise. Thus, for example, reference to "a reservoir" includes one or more of such spaces and reference to "filling" includes reference to one or more of such steps.

The osmotic pump as for instance shown in the accompanying Figures may comprise a first chamber 8 and a second chamber 15 which are separated from each other by a semi-permeable membrane 14. The first chamber 8 can be and is typically filled with an osmotically active substance which forms together with a solvent an osmotic agent 18. The osmotic agent is typically a solution containing the osmotically active substance which is either completely or partially solved therein. Typically, the osmotically active substance is provided in such a quantity that it can only partially be solved in the available solvent. This ensures that even under operation of the osmotic pump the osmotic agent 18 remains a saturated solution which keeps the osmotic pressure difference across the semi-permeable membrane 14 stable. As described in detail below, reference sign 19 denotes unsolved particles of the osmotically active substance.

If an aqueous solvent is used, the osmotically active substance can be for examples a salt such as NaCl, KCl, $CuSO_4$, $KClO_4$, an organic macromolecule such as a polyelectrolyte like sodium polystyrol sulfonate, poly-diallyldimethyl-ammonium chloride, polyacrylic acid or a neutral polymer like polyethylene glycol or a dextrane. Alternatively, other solvents such as ethanol, dioxane, acetone, chloroform can also be used. Suitable osmotically active substances for such solvents are soluble organic polymers such as polystyrol or polyethylene glycol. The semi-permeable membrane is selected depending on the solvent and the osmotically active substance. For example, when using water as solvent and a low molecular osmotically active substance such as NaCl, typically a reverse osmosis membrane or a porous membrane made of polypropylene, polytetraflouroethylene or other hydrophobic materials is used. When using an osmotically active substance having a large molecular weight such as polyethylene glycol, polystyrol sulfonate, dextran sulfate, other semi-permeable membranes such as dialysis and ultrafiltration membranes comprising cellulose acetate membranes, polyether sulfone membranes, ceramic and silicon membranes can be used as well.

When the second chamber 15 is filled with a solvent 17 for the osmotically active component, the osmotic potential difference between the first and the second chambers 8, 15 drives a solvent flow across the semi-permeable membrane 14 from the second chamber 15 into the first chamber 8. This causes a volume increase of the osmotic agent 18 which can be used either directly or indirectly by displacing a pumped fluid 10. To this end, the osmotic agent or solution 18 is separated from the pumped fluid 10 by a movable barrier 5 which is impermeable to the osmotic agent 18 and the pumped fluid 10. The movable barrier 5 can be for instance a flexible and/or deformable membrane or a solid barrier which is displaceably arranged. The osmotic solution 18 is referred to as driving fluid.

When using a flexible and/or deformable membrane as movable barrier, the membrane can be for example comprised of polypropylene, polyethylene, poly-tetraflouorethylene, polyurethane, cycloolefin polymeres, nitrile butadiene rubber, polyvinyl chloride, silicone rubber, latex rubber and the like.

The second chamber 15 is in fluid communication with a pressure device 60 which is arranged to provide a pressure on the solvent 17. Pressurizing the solvent 17 keeps it in permanent contact with the semi-permeable membrane 14 so that the entire surface of the semi-permeable membrane 14 separating the first chamber 8 from the second chamber 15 is wetted by the solvent 17. This maintains the solvent flow through the semi-permeable membrane 14 at its designated flow rate. Since a pressure is applied to the solvent 17, the osmotic pump can be operated under any conditions and orientation including mobile applications, at zero gravity or under acceleration forces. The pressure device 60 is therefore adapted to provide sufficient pressure with respect to the ambient to keep the solvent 17 in contact with the semi-permeable membrane 14. For example, a pressure difference to ambient of about 0.2 bar or higher has been shown to be sufficient. Typically, the pressure, which is substantially permanently provided by the pressure device can be in a range from about 0.5 bar to about 5 bar with respect to ambient. The pressure provided also helps to immediately start the osmotic pump. The pressure device 60 therefore can be arranged to provide a permanent base pressure on the solvent which can be at least 0.2 bar or more with respect to ambient.

The second chamber 15 can either be at least partially flexible or substantially incompressible under consideration of the pressure differences occurring during operation of the osmotic pump. For example, in case of a flat polymer membrane forming the second chamber, the walls are rather flexible and the chamber collapses when the back pressure of the application is higher than the pressure deriving from the pressure device 60. In this description, the term "back pressure" describes the pressure against which the osmotic pressure works, for instance to pump fluid through tubing or to do work. The pressure of the pressure device 60 can be equal to or higher than the back pressure of typical applications to avoid collapse of the second chamber 15. A tubular shape of the chamber 15 also contributes to its rigidity. Alternatively, the walls of the second chamber can be made rigid or a rigid support for the membrane 14 can be supplied to sustain the pressure difference even when no additional solvent is delivered. In this case, the solvent degases due to the underpressure in the second chamber so that the second chamber becomes filled with gas.

In an embodiment, the osmotic pump is connected to a fluidic device which requires a minimum pressure. To avoid collapsing of the second chamber 15 or to support the membrane 14, the pressure device 60 is arranged to provide a pressure which is at least equal to and typically higher than the minimum pressure of the fluidic device. The minimum pressure of the fluidic device corresponds here to the back pressure.

The designated flow rate is particularly defined by the total surface area of the membrane 14 and its permeability with respect to the solvent 17. If for instance gas bubbles are contained within the second chamber 15 which partially block or cover portions of the semi-permeable membrane 14, the actual flow rate can be reduced, in particular if the semi-permeable membrane 14 comprises a hydrophobic porous membrane. Gas bubbles may origin from the solvent 17 which may partially degas in the second chamber 15 or are left as residue from the filling process. Gas bubbles may also be generated by cavitation within the second chamber 15 when an underpressure is generated within the second chamber due to the osmotic action of the osmotically active substance. The pressure applied to the solvent 17 helps to minimise formation of gas bubbles and to force complete wetting of the semi-permeable membrane 14 or to eliminate residual gas bubbles. If at least a portion of or the complete semi-permeable membrane is comprised of a gas-permeable material, the gas bubbles will be pushed therethrough and removed. Alternatively or additionally, an air vent can be used which is in fluid communication with the second chamber 15 typically at its down-flow side.

The pressure generated by the pressure device 60 should be significantly smaller than the osmotic potential of the applied osmotic active substance (18) so that any variation of the pressure generated by the pressure device 60 does not significantly affect the total flow rate of the osmotic pump. In exemplary embodiments, pressure device 60 may deliver a pressure between about 0.5 bar and about 2 bar with respect to ambient. For comparison, a saturated NaCl solution can osmotically generate a maximum pressure of about 374 bar at room temperature. Hence, the pump rate of the osmotic pump as described herein is mainly defined by the flow of solvent due to the osmotic action. The pressurized solvent 7 only slightly affects the flow rate. However, when bypassing the membrane as described in some embodiments, the pressure device mainly determines the flow rate which can be significantly higher than the osmotically determined flow rate.

In certain exemplary embodiments, the pressure device 60 can comprise an energy storage which provides energy for pressurizing the solvent 17. Typically, the energy storage is rechargeable to allow repeated use. The energy storage ensures that the osmotic pump can be used independently from any additional energy supply which is particular of advantage for mobile applications and disposable osmotic pumps. While any energy storage can be used in principle, typically a storage for mechanical energy is used which allows easy conversion of the energy into a pressure acting on the solvent 17. For example, the energy storage may store energy such as mechanical or chemical energy in any suitable form such as by compressing or tensing a spring, compressing a gas, vapour pressure of a volatile liquid, a swelling hydrogel, or other pressure generating means. In certain embodiments described hereinafter, the energy storage is a pressure storage. Other embodiments make use of releasable chemical energy.

In further exemplary embodiments, the energy storage comprises a movable member 4, 38 for acting on the solvent. The movable member is driven by the energy released from the energy storage to do work on the solvent. The energy stored in the energy storage is transformed into a pressure by the movable member which can be a displaceable member, such as a plunger, or an elastic or flexible member or barrier.

The pressure device is position-independent, which means that its position, location or orientation with respect to the second chamber 8 does not substantially influence the pressure exerted on the solvent unlike for example means using a position-dependent hydrostatic pressure generated by gravity. The pressure device of the osmotic pump described herein is superior to those means since it allows permanently pressurizing the solvent and opens many options for using the osmotic pump. The pressure is therefore generated by the pressure device by means different to the hydrostatic pressure of the solvent caused by gravity. The osmotic pump can therefore be used in any orientation, location or situation such as upright or up-side down and under the influence of external forces or at zero gravity since the pressure device is gravity-independent.

As described in detail below in connection with various embodiments, the pressure device 60 may comprise a third and a fourth chamber 7 and 6 which are separated from each other by the movable member 4, 38. The third chamber 7 is in fluid communication with the second chamber 15 and is filled with the solvent 17. The fourth chamber 6 comprises the energy storage that at least partially and gradually releases its energy through the movable member 4, 38 which exerts a pressure on the solvent 17 contained in the third chamber 7.

In further exemplary embodiments, a valve is located between the pressure device 60 and the second chamber 15 in order to permit or inhibit the solvent 17 to contact the semi-permeable membrane. This provides for a control of the osmotic pump by switching the solvent flow to the semi-permeable membrane.

In other exemplary embodiments, the osmotic pump comprises a bypass between the first and the second chambers 8, 15 for bypassing the semi-permeable membrane 14. The bypass can be selectively activated and deactivated by a control valve. The valve is deployed to permit or inhibit a bypass flow of the solvent 17 into the first chamber 8 of the osmotic pump without passing the semi-permeable membrane 14.

The osmotic pump described herein can be switched on and off instantly without a substantial delay of operation due to the substantially permanently applied pressure. "Substantially permanently applied" means that interruptions may occur, for instance during switching of valves or a temporal disconnection of the second chamber from the pressure device as described below. Furthermore, the osmotic pump can provide different flow rates between which one can easily select and switch. Another advantage is that the osmotic pump is capable of delivering an extra bolus of fluid on demand. Therefore, the osmotic pump is switchable.

A specific embodiment of an osmotic pump comprises at least a reservoir 8 forming the first chamber 8 and containing the osmotic agent 18, a reservoir 7 forming the third chamber 7 for the solvent 17 and a membrane 14 forming the semi-permeable membrane that is impermeable to the osmotic agent 18 but permeable to the solvent 17 in either liquid or gaseous or both states of matter. One side of said membrane 14 is in contact with the osmotic agent 18 and the other side of the membrane 14 is in contact with a cavity 15 forming the second chamber that can be filled with solvent 17. The reservoir 7 for the solvent 17 is bordered at least partially by a movable, flexible or elastic barrier forming the movable member 4, 38 for transducing a pressure to the reservoir 7 at least when the reservoir 7 is filled at least partially with solvent 17. The osmotic pump with its pressure device 60 can be integrally formed in cavities of a solid material as described below.

Figure 1B:
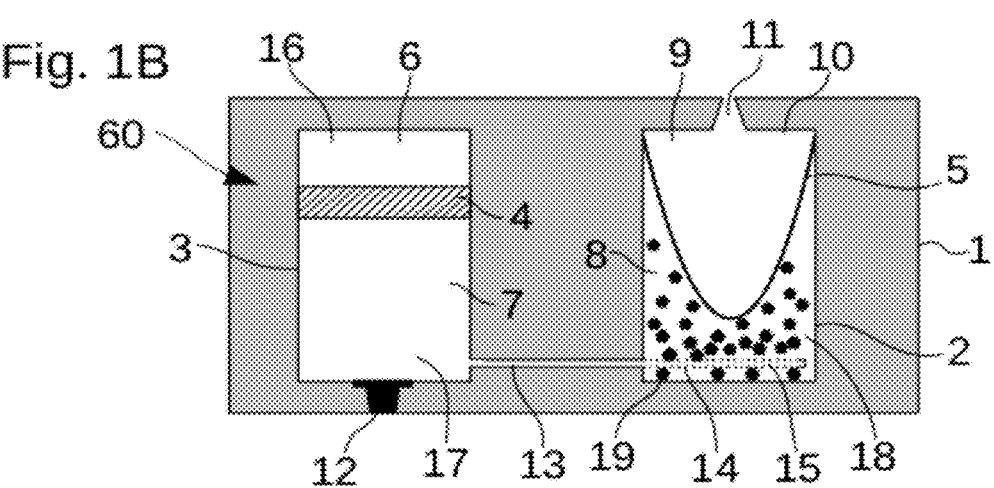
Figure 1C:
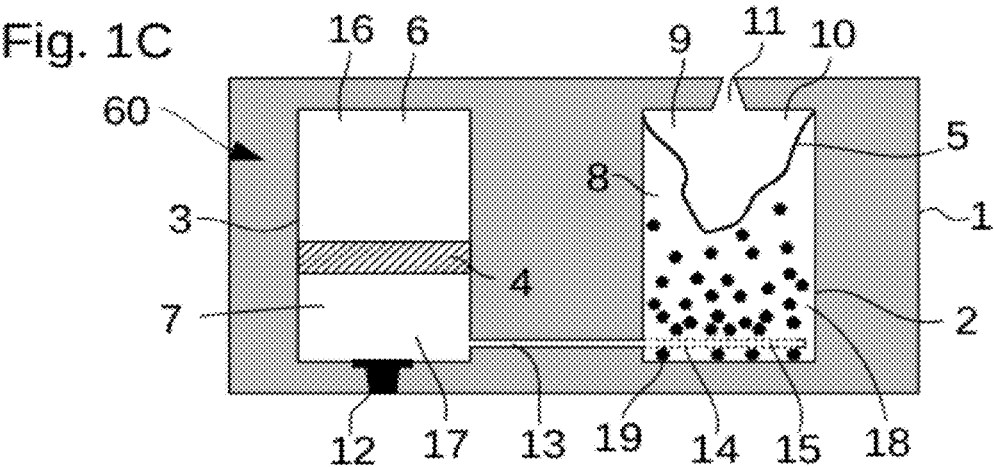

FIGS. 1A to 1C illustrate an embodiment of an integrated osmotic pump comprising all chambers in a common housing 1 formed by a solid material. The housing 1 comprises a first cavity 2 and a separate second cavity 3. First cavity 2 accommodates the first and second chambers 8 and 15 while second cavity 3 comprises the pressure device 60 with its third and fourth chambers 7 and 6, respectively. Third chamber 7 forms reservoir 7 while first chamber 8 forms reservoir 8. Membrane 14 is arranged in the first cavity 2 and encloses the second chamber 15 which is in this embodiment a tube of a semi-permeable material extending into the first cavity 2. Second chamber 15 is connected to the reservoir 7 for the solvent 17 by a channel 13. It is apparent, that the reservoirs could also be constructed in different housings and the connection made by tubings. The embodiment of FIGS. 1A to 1C also shows a reservoir 9 for a pumped fluid 10. The reservoir 9 is separated from reservoir 8 by a flexible or elastic impermeable barrier 5. It could as well be separated by any other impermeable movable barrier, like a plunger. The pumped fluid 10 is pumped out through an orifice or outlet 11. In this embodiment, reservoirs 8 and 9 are placed in the same cavity 2. It is apparent, that the reservoirs could also be constructed in different cavities or different housings and coupled by channels or tubings. First chamber 8 is filled with a solid osmotically active substance 19 suspended in its saturated solution forming the osmotically active agent 18. In this embodiment, third chamber 7 further comprises a filling port 12 that can be used to fill solvent 17 into the third chamber 7. When filling the third chamber 7 with the solvent 17, the movable member 4, which is arranged in the second cavity 3 and separates third chamber 7 from fourth chamber 6, can be displaced which results in a reduction of the volume of the fourth chamber 6 and a compression of a fluid contained therein. Typically, the fluid is a gaseous media 16 enclosed therein. The fluid or gas 16, which forms in this embodiment the energy storage, can be pre-pressurized to ensure that it is under pressure even at maximum expansion so that it permanently exerts a sufficiently high pressure onto the movable member or barrier 4 at all positions of the moveable barrier 4. The movable barrier 4 transduces pressure form the pressurized gas 16, e.g. air, to the solvent 17. Therefore, it is ensured that the solvent 17 gets in contact with the membrane 14 immediately after filling chamber 7 with solvent 17, and remains in contact therewith securely during operation of the osmotic pump. The pressure on the solvent 17 is maintained until the movable barrier 4 is displaced to its maximum location.

FIG. 1A shows the osmotic pump with solid osmotic agent 19 forming together with solvent 17 a saturated solution 18 which is filled in reservoir 8 (first chamber) and fluid 10 to be pumped filled in reservoir 9. The osmotic pump can be stored in this state for indefinite periods of time. Alternatively, the osmotic pump can be stored with chamber 9 being empty and to be filled just before use. Alternatively, the osmotic pump may not comprise fluid chamber 9, and an extra chamber for a pumped fluid can be optionally connected to chamber 8 by tubing.

FIG. 1B shows the osmotic pump after third chamber 7 was filled with solvent 17 through filling port 12. Since the pressure generated by the compressed media 16, which is typically a gaseous fluid, in chamber 6 forces solvent 17 to contact membrane 14, the osmotic pump starts to deliver fluid at its designated flow rate immediately after filling chamber 17.

FIG. 1C shows the osmotic pump some time after the pump was started. In this situation, the solvent that is imbibed osmotically into first chamber 8 leads to partial dissolution of solid particles of osmotically active substance 19 which keeps the osmotic agent 18 saturated. As a result, the flow rate remains constant as long as unsolved solid particles 19 are still present. The amount of solid particles 19 can be chosen such that osmotic pressure differences across the membrane 14 remains substantially constant to keep the flow rate constant during operation of the pump or such that a declining flow rate during operation from the beginning or after a determined time of operation can be obtained.

According to another exemplary embodiment, the solvent 17 is pressurized by means of a spring 22 acting on the movable impermeable barrier 4. Spring 22 forms here the energy storage which is here a pressure generating means. A valve 23 arranged in channel 13 formed by channel portions 24 and 25 permits or inhibits solvent 17 to be pushed into the second chamber 15 bordered at least partially by the membrane 14. The osmotic pump of this embodiment can be stored with solvent 17 filled in reservoir 7 (third chamber 7) and valve 23 closed. The osmotic pump starts immediately after valve 23 is put to an open position, permitting the pressurized solvent 17 to be pushed to the membrane 14. The osmotic pump can be stopped at any time and repeatedly during operation by putting valve 23 to a closed position. When the valve 23 is closed, the pump will stop after the amount of solvent remaining between the valve 23 and the membrane 14 is substantially imbibed by the osmotic agent 18. This means that the osmotic pump may comprise a lag volume which is emptied before the osmotic flow stops. The lag volume is defined by the second chamber 15 and the portion 25 of channel 13. On the other hand, it may happen that not all of the solvent in the second chamber is imbibed, for instance due to the formation of air bubbles by cavitation which can inhibit a further solvent flow through the semipermeable membrane. In this case, solvent may partially remain in the second chamber 15 or channel portion 15 which effectively reduces the lag volume. Furthermore, cavities 26 and 27 may also contribute to the lag volume if present. The function of cavities 26 and 27 will be described below. If these cavities and chambers are designed to be very small, the pump will stop shortly after the valve 23 is closed.

Figure 2A:
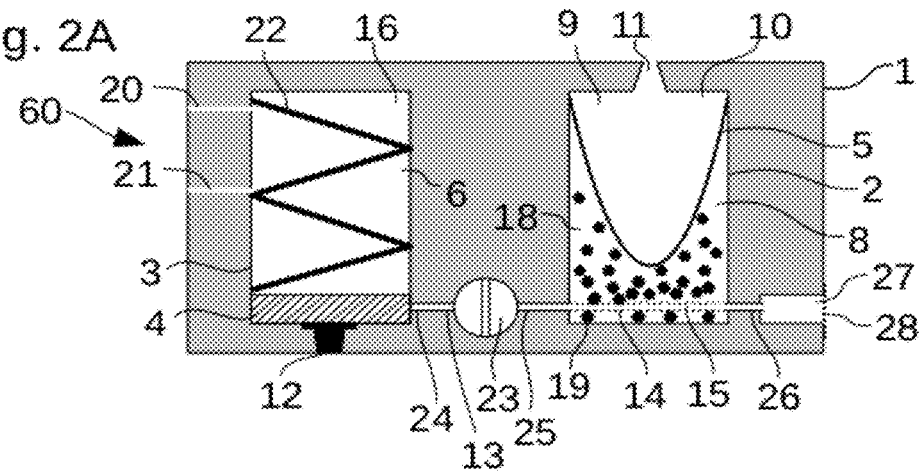
FIGS. 2A to 2C show another embodiment of an osmotic pump at different phases of operation.
Figure 2B:
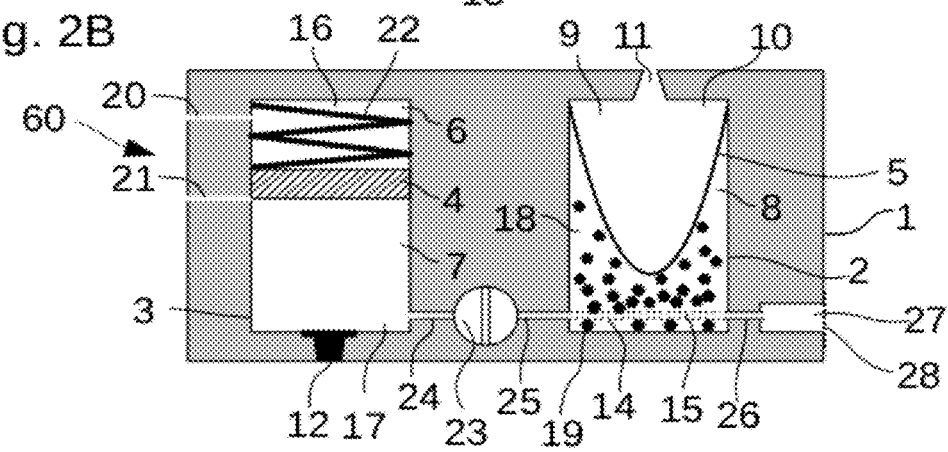
Figure 2C:
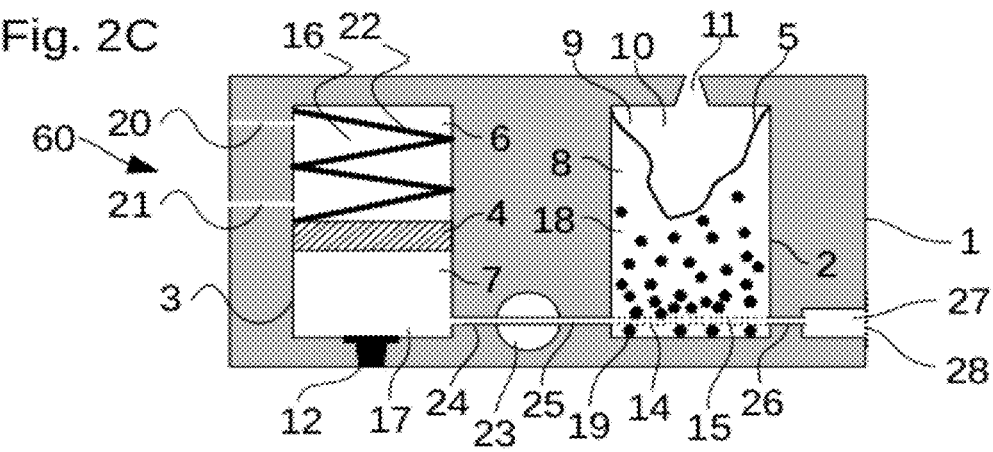

FIGS. 2A to 2C illustrate an embodiment of an osmotic pump wherein the reservoir 7 for the solvent 17 is pressurized by means of spring 22. FIG. 2A shows the osmotic pump prefilled with a suspension of solid osmotically active substance 19 in its saturated solution 18 in reservoir 8 and with pumped fluid 10 in reservoir 9. Reservoir 7 is not prefilled. FIG. 2B shows the osmotic pump after solvent 17 was filled into reservoir 7 through filling port 12. The filling process can be performed e.g. by a common syringe if filling port 12 consists of a self closing needle plug or a needle free Luerport. While filling reservoir 7 with solvent 17, the movable impermeable barrier 4 is moved and the spring 22 is tensed. Spring 22 can also be compressed by other means such as a pushing rod to reduce the pressure required to fill the solvent into reservoir 7. The air 16 can exhaust from cavity 6 (fourth chamber) through a bore 20 which is arranged such to allow air to leave the second cavity 3 at each position of the movable barrier 4. The maximum amount of solvent 17 filled into reservoir 7 can be defined by the location of a second bore 21 which can be at any intermediate position between the maximum and minimum position of movable barrier 4. If the movable barrier 4 passes second bore 21, any extra amount of filled solvent 17 leaves the reservoir 7 through second bore 21. Residual air can also easily be flushed from reservoir 7 through second bore 21. The osmotic pump as shown in FIG. 2B can be stored completely prefilled ready to use for indefinite time. It starts to run at its designated flow rate immediately after valve 23 is put to an "open" position, connecting the second chamber or cavity 15 bordered by the membrane 14 to the pressurized reservoir 7.

FIG. 2C shows the osmotic pump some time later during the pumping process. Here, according to the pumping process, the amount of solvent 17 and pumped fluid 10 has declined and the amount of driving fluid 18 has increased. The pumping process can be interrupted repeatedly by means of valve 23.

The embodiment illustrated in FIGS. 2A to 2C additionally comprises an optional venting appliance or air vent to vent air or gas that might be present in the cavity 15 (second chamber) and could hinder solvent 17 from contacting the membrane 14 on its entire surface. The venting appliance comprises a cavity 27 that is coupled in fluid communication with second chamber or cavity 15 by a channel 26 and is bordered by a venting membrane 28. Appropriate venting membranes are made for example from porous hydrophobic material such as polypropylene and polytetraflouroethylene. They permit the passage of gas and prevent the passage of aqueous liquids. Therefore, residual gas from cavities 15 and 27 and channel portions 25 and 26 is displaced completely by inflow of solvent 17 when valve 23 is put to an "open" position. If no venting compartment is applied, gas can be securely displaced from cavity 15 through membrane 14 into reservoir 8 if the membrane 14 is at least partially or completely comprised of hydrophobic porous material. Appropriate membranes are widely available and are made form polypropylene, polytetrafluoroethylene and other hydrophobic polymers. In either case, any gas or air that might be present in the solvent 17 can be removed from the second chamber 15 through a respective gas-permeable barrier.

Figure 3A:
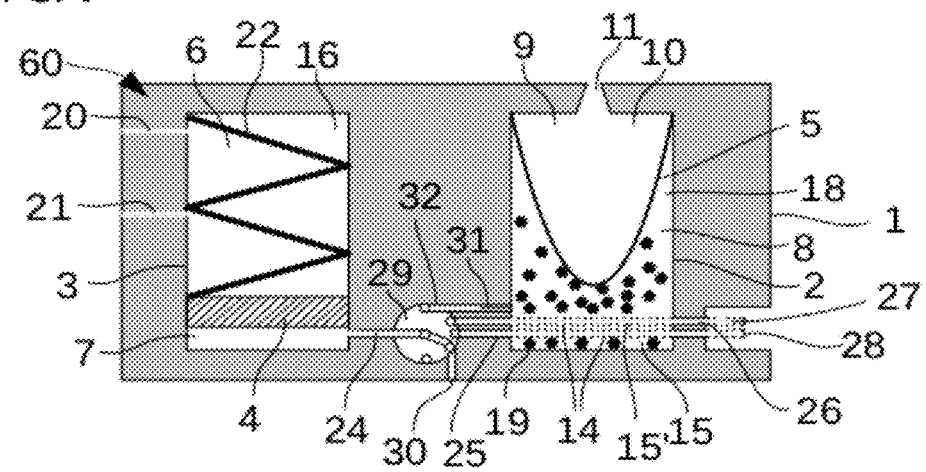
FIGS. 3A to 3D show a further embodiment of an osmotic pump at different phases of operation.

In order to provide different flow rates, the osmotic pump of certain exemplary embodiments may comprise multiple cavities forming separate second chambers 15 of the same or different volumes bordered by similar or different membranes 14 with similar or different surface areas. As illustrated in FIG. 3A, a multiple port valve 29 can be applied to select which chamber or cavity, if at all, is connected with the pressurized reservoir 7. Different preset flow rates of the osmotic pump can be selected during operation thereby. An additional channel 32 forming a bypass and connecting an outport of valve 29 with the first chamber or reservoir 8 can be applied to enable a direct fluid connection of reservoir 7 with reservoir 8 to bypass the semi-permeable membrane 14 in order to achieve very high flow rates which are determined by the pressure existing in reservoir 7. In this case, the pressure device 60 is used to pump solvent 17 directly into the first chamber 8 which causes displacement of the pumped fluid in reservoir 9. The obtainable pump rate is determined by the pressure of the pressure device 60 and the hydraulic resistance of channels 24 and 32 and can significantly exceed the pump rate defined by the osmotic action. Bypassing the semi-permeable membrane 14 as described herein can be useful e.g. to flush tubing connected to the outlet 11 of the pump in advance of operation or during regular operation of the pump. In order to pre-define a flow rate achieved by means of channel 32, an adequate flow resistor 31 can be implemented in or connected to channel 32 or channel 24.

Moreover, the valve 29 can also provide access to the reservoir 7 via a filling port 30 in order to enable secure filling or refilling of solvent 17.

FIGS. 3A to 3D illustrate different phases during use of the osmotic pump having a multi-port valve 29 which enables the connection of the reservoir 7 with a bypass channel 32 having a flow resistor 31 embedded within, several membrane-bordered cavities or second chambers 15, 15', and a filling port 30. In this particular embodiment, two second chambers 15, 15' are used, each of which is formed by a hollow fibre comprised of a semi-permeable membrane.

Figure 3B:
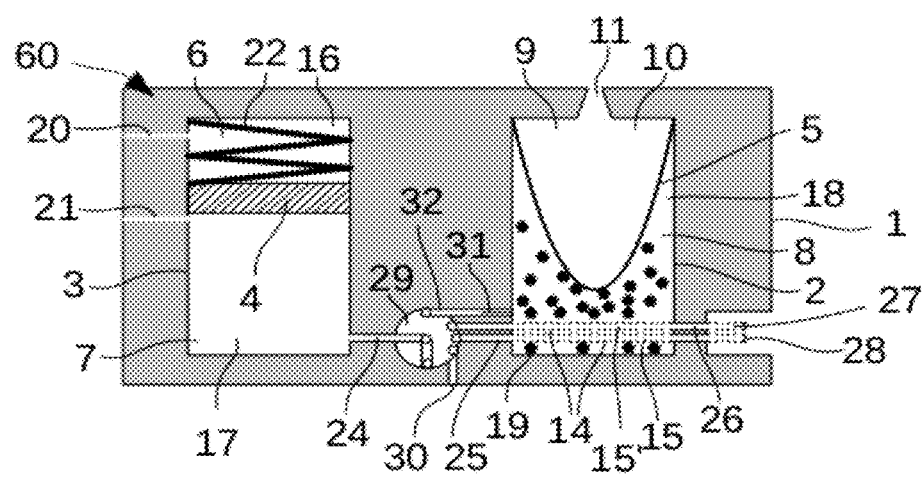

In FIG. 3A the reservoir (third chamber) 7 is empty. It is connected with the filling port 30 via valve 29. FIG. 3B illustrates the pump after reservoir 7 was filled with solvent 17 through filling port 30 and afterwards the valve 29 was set to a "closed" position. The pump can be stored in this state ready-to-use.

Figure 3C:
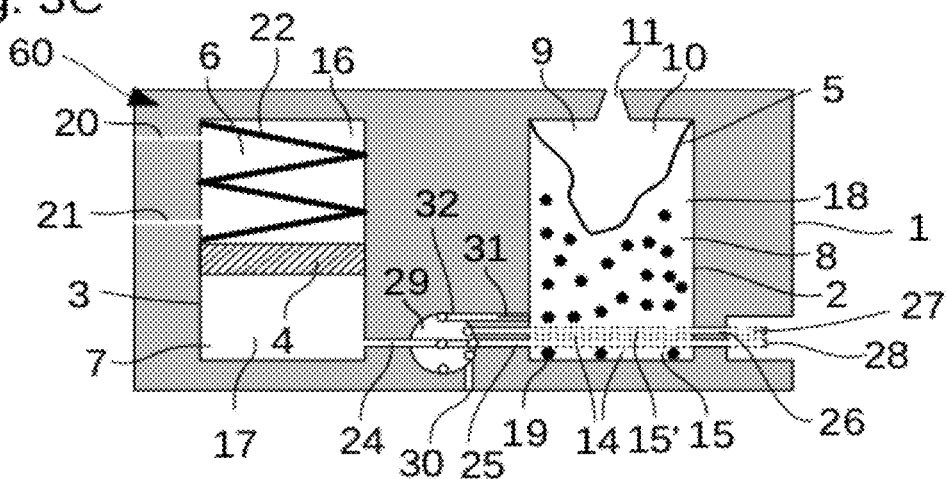
Figure 3D:
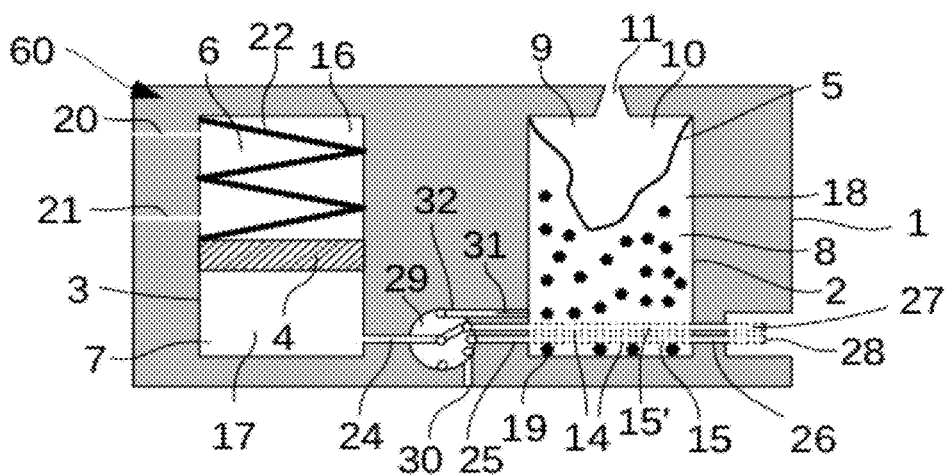

FIG. 3C shows the pump in a working phase with the reservoir 7 connected with one of the cavities (second chambers) 15 via valve 29 and therefore pumping at a determined flow rate. In the phase illustrated in FIG. 3D the pump is running at a different flow rate defined by the properties of another second cavity 15' connected with reservoir 7 via valve 29. Second chambers 15, 15' may have different surface areas or different semi-permeable membranes and may therefore provide different flow rates.

It has to be mentioned that the osmotic pump delivers a higher flow rate for a short time after switching valve 29 from one cavity 15 to another cavity 15'. The reason is, that the connected cavity 15' will start to pump almost immediately while the disconnected cavity 15 will continue pumping until the remaining amount of solvent 17 in the disconnected cavity is substantially completely imbibed by the osmotic pump through the adjacent membrane 14. This effect can be almost eliminated by minimising the volume of the respective cavities 15, 15'.

On the other hand, the effect can be used to provide bolus dosages of the pumped fluid 10. Given bolus volumes at defined flow rates can be achieved repeatedly by adequate design of the cavities 15, 15' in respect to cavity volume and membrane surface area and properties. Bolus dosage can be triggered by actuation of valve 29 or by means of an additional valve connected to the reservoir 7 and an additional bolus-giving cavity 15. For example, one of the cavities (second chambers) 15, which is referred to as base cavity and which is connected with reservoir 7, delivers a base flow rate of about 0.5 µl/min. Connecting the other cavity 15', which is referred to as bolus-giving cavity and has a volume of about 10 µl, with the reservoir 7 via valve 29 for a short time causes solvent to be pushed into this cavity. The valve 29 then returns to its initial position for connecting the base cavity with reservoir 7. Since the bolus-giving cavity 15' is now filled in addition to the base cavity 15, both contribute to the total osmotic flow with the flow of the bolus-giving cavity 15' providing an extra flow on top of the base flow. The flow rate of the bolus-giving cavity can be for example 1 µl/min. Therefore the total flow rate of the osmotic pump is approximately 1.5 µl/min for approximately 10 minutes before it returns to the base flow rate of 0.5 µl/min. It goes without saying that two or more separate valves can be used instead of or in addition to the multi-port valve.

Another embodiment of the present invention employs a bypass channel 36 between the downstream side of cavity 15 bordered by the membrane 14 and the reservoir 8. The bypass channel 36 can be closed by means of a valve 61. The exemplary embodiment illustrated in FIGS. 4A to 4C comprises a second or outlet valve 35 to permit or inhibit elusion of pumped fluid 10. Valve 35 can e.g. be a luer-activated valve that is in "open"-condition when a male luer connector is attached and in a "closed"-condition when no connector is attached.

In this embodiment, a spring 22 is used as energy storage and the movable member 4 is formed for instance by a plunger which comprises a self-sealable filling port 37 substantially coaxially aligned with a bore 34 in housing 1 through which a syringe 33 can be inserted with its tip inserted into the filling port 37. The spring 22 can be tensed by any suitable means. With the spring 22 tensed and the plunger pushed upwards the reservoir 7 of the pressure device 60 is filled through filling port 37. Alternatively, spring 22 can be tensed by filling the reservoir 7 with solvent which causes displacement of the plunger 4 and compression of the spring 22. Filling the reservoir 7 with the bypass valve 61 in an opened position concomitantly allows filling of cavity 15 and bypass channel 36 through channel 13 and, since this may cause an volume increase in reservoir 8, also of tubings connected with outlet valve 35 if it is opened. It goes without saying that the syringe 33 is removed after filling reservoir 7.

Figure 4A:
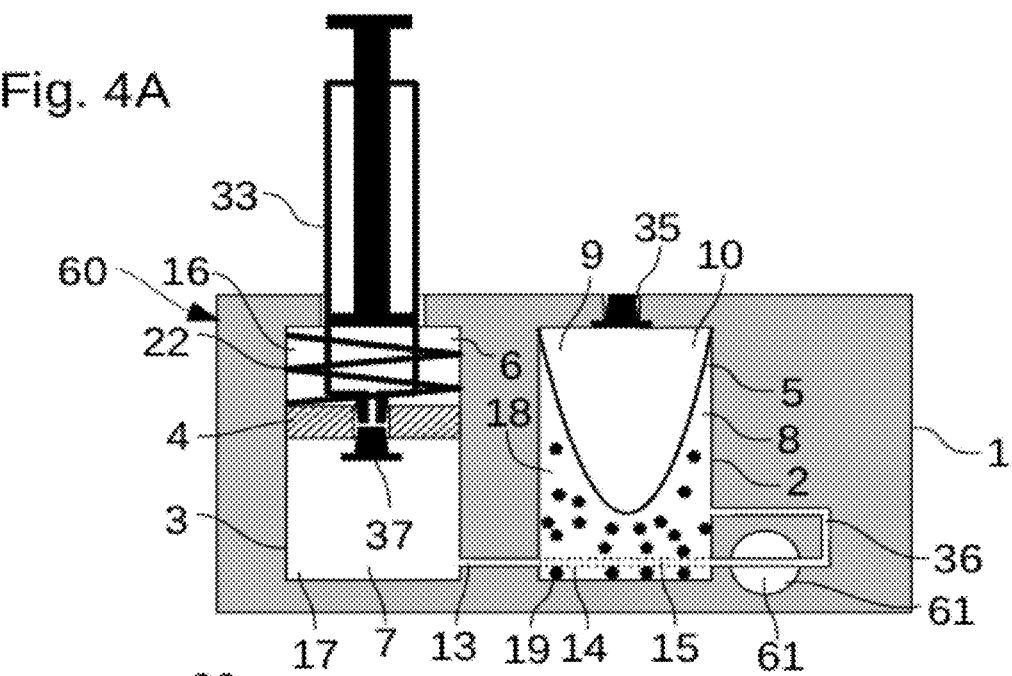
FIGS. 4A to 4C show yet another embodiment of an osmotic pump at different phases of operation.

The phase of the osmotic pump illustrated in FIG. 4A shows outlet valve 35 closed and bypass valve 61 in an "open" position. Solvent 17 that is present in cavity 15 is osmotically imbibed through the membrane 14 into reservoir 8. Since the bypass channel 36 is the only opening where the imbibed volume can pass off, the imbibed solvent from cavity (second chamber) 15 is replaced by the solution of the osmotic agent 18 by a convective flow through bypass channel 36. It is important to understand that only the cavity 15, reservoir 8, bypass channel 36 and the valve 61 are affected of this convective flow. There is no convective flow in channel 13, in reservoir 7 and in reservoir 9. After a short while, all affected compartments are filled with osmotic solution 18. Therefore the osmotic gradient across the membrane 14 decreases to zero and the convective flow is stopped.

Channel 13 and reservoir 7 may be affected by diffusion of osmotic agent in this phase of operation. Diffusion into reservoir 7 can be reduced by increasing the length and decreasing the cross-section (diameter) of the connecting channel 13. Since diffusion is an extremely slow process, the osmotic pump of FIGS. 4A to 4C can be stored in the phase illustrated in FIG. 4A for several months without noteworthy contamination of the solvent 17 by osmotic agent 18. Alternatively a valve can be deployed to prevent contamination of solvent 17 in reservoir 7.

Figure 4B:
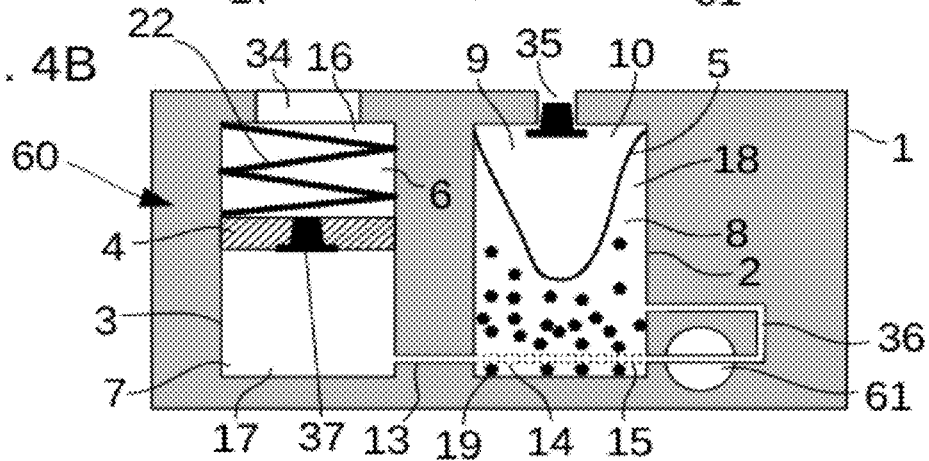
Figure 4C:
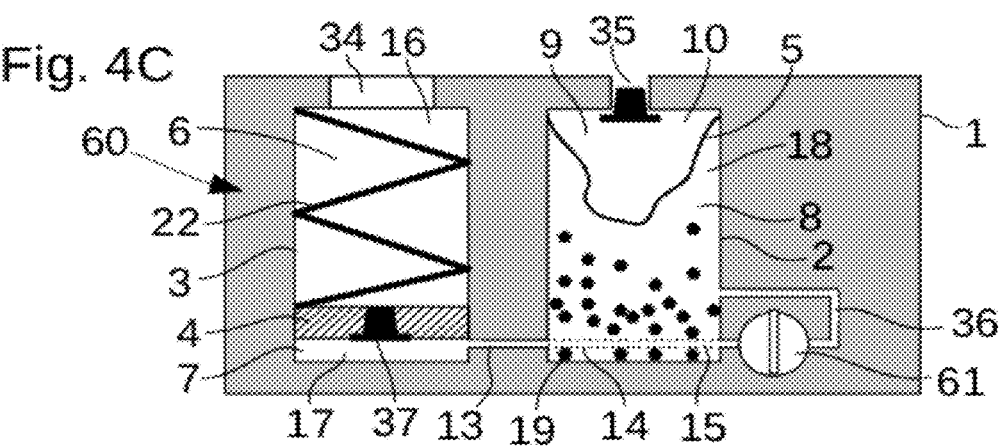

The pump shown in FIG. 4A can be started at a high flow rate immediately when outlet-valve 35 is opened as illustrated in FIG. 4B. Valve 35 can for instance be opened automatically when tubing is connected. Direct connection of the pressurized reservoir 7 to the reservoir 8 by the open valve 61 and the bypass channel 36 allows simultaneous flushing of the connected tubing with pumped fluid 10 and flushing of the channels 13, 36, the cavity 15 and the valve 61 with solvent 17. After the system is flushed with a desired total volume of fluids, the valve 61 is set to a "closed" position as shown in FIG. 4C. Henceforth the pump is working by means of osmosis only. An extra flush can be provided repeatedly during operation by switching the valve 61 to an "open"-position for a desired period of time. As an example, the osmotic flow rate can be about 0.3 µl/min whereas the flow rate during flushing can be about 150 µl/min depending on the pressure provided by the pressure device 60 and the hydraulic resistance of the fluid connection through valve 29 between reservoir 7 and reservoir 8.

It is an advantage of the osmotic pump illustrated in FIGS. 4A to 4C that the pump can be designed to start automatically when tubing is connected.

It is another advantage of the osmotic pump illustrated in FIGS. 4A to 4C that it can be stored with all compartments of the fluidic pathway filled with liquid media. Therefore no gas bubbles occur that have to be vented or otherwise contribute to an unwanted elasticity of the pumping device.

Figure 5D:
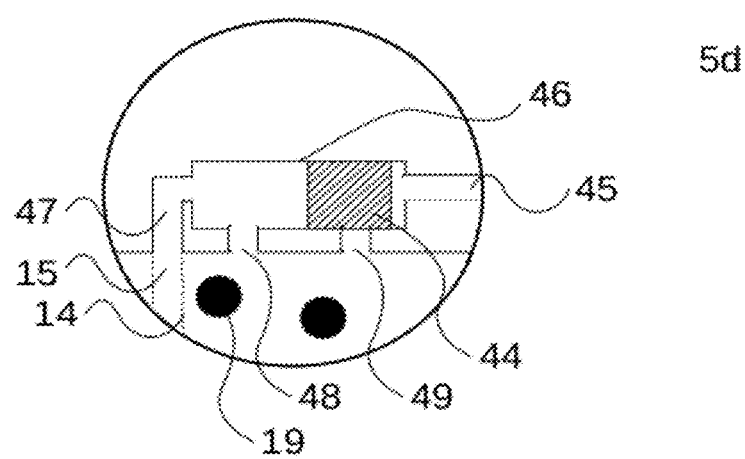

This can also be achieved in an exemplary embodiment using one valve only as illustrated in FIGS. 5A to 5F. FIG. 5A shows the pump in a stopped or "parked" state. A four port valve 46, which is illustrated in detail in FIGS. 5D to 5F in different positions corresponding to the situations shown in FIGS. 5A to 5C, is deployed with its outlet port 45 closed by a piston or spool 44, thereby opening a bypass between cavity 15 and reservoir 8 through valve inlet 47 and valve port 48. In this situation, as described before, the osmotic potential difference across the membrane 14 will therefore become zero and the pump will stop. The piston or spool 44 of valve 46 has three possible positions each being shown in one of the FIGS. 5D to 5F.

Figure 5E:
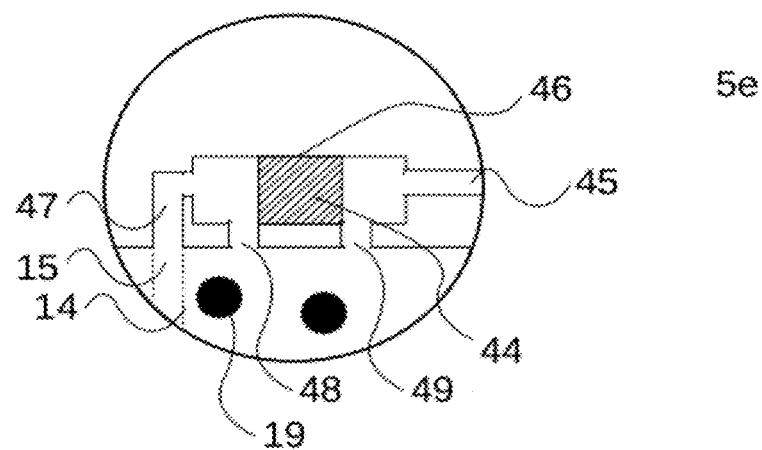
Figure 5F:
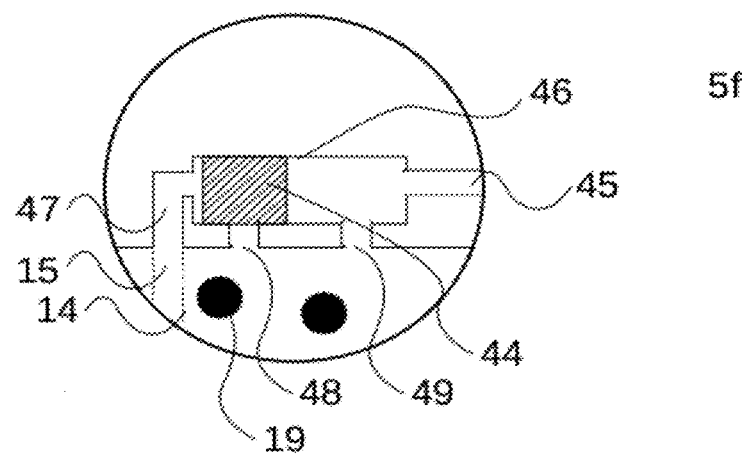

FIG. 5B and corresponding FIG. 5E illustrate the osmotic pump during a flushing phase. Here, all ports (inlet port 47, outlet port 45, valve ports 48 and 49) are opened, and pressurized solvent 17 is being flushed through channel 13, cavity 15, inlet 47 and valve port 48 into reservoir 8 by action of pressure device 60. Osmotic agent 18 is, accordingly, flushed through valve port 49 and outlet port 45. When the valve inlet 47 is closed as illustrated in FIGS. 5C and 5F, the osmotic pump will deliver at its basic osmotic flow rate as described before.

Moreover, the embodiment of FIGS. 5A to 5F comprises a third cavity 40 in fluid communication with the outlet of the reservoir 8 (third chamber) through valve 46. The pumped fluid 10 is arranged in the third cavity 40 in an extra pouch 42 formed by a flexible or expansible material. Here the driving fluid 18 (osmotic agent) is pumped into a compartment 41 within the third cavity 40 in order to pressure the pouch 42 and thereby displace pumped fluid 10 through a fluid outlet 43. In this embodiment, compartment 41 is defined to be space within the third cavity 40 which is not assumed by pouch 42.

The embodiment of FIGS. 5A to 5F has the advantage that a separate pre-filled removable pouch can be used to provide a pumped fluid 10 rather than filling a reservoir within the pump with pumped fluid. This is of special interest if the pumped fluid 10 has a short shelf life or if it needs to be sterile which can be done separately to the osmotic pump.

The first, second and third cavities 2, 3 and 40 are formed within the same solid material to define an integrated osmotic pump. Optionally, all or only some cavities can be formed in separated housings and materials. Integrating all cavities within one housing provides the advantage of miniaturising the osmotic pump which is useful for instance for disposable osmotic pumps.

Different means to pressurize the solvent 17 have been described and illustrated. Yet another option is to fill the reservoir or cavity 6 at least partially with a volatile liquid that generates a sufficient vapour pressure inside cavity 6 at the pump's operating temperature. It is an advantage of this embodiment that the pressure remains constant at constant temperatures, independent of the charging level of cavity 6 or reservoir 7. It is another advantage, that the cavity 6 can be very small in respect to the volume of reservoir 7. Another advantage is, that the pressure generating volatile liquid can be filled in after filling of reservoir 17. The solvent-filling process can, therefore, be carried out under ambient pressure.

The exemplary embodiment of FIGS. 5A to 5C illustrate a pressure device forming a pressure generating means comprising such a volatile liquid 50, an impermeable movable barrier 38 and a filling port 39. The volatile liquid can be e.g. liquid propane, liquid butane, a mixture of liquid butane and pentane or other volatile liquids and mixtures thereof. The volatile liquid 50 is filled into reservoir 6 through filling port 39. It generates a sustainable pressure onto the movable barrier 38 and thereby pressurizes the solvent 17 in reservoir 7.

Alternatively, reservoir 6 can be filled with a hydrogel which swells upon bringing in contact with an aqueous solution.

Basically, any energy storage forming a pressure generating means can be used and the particular embodiments described herein are not restricted to the shown pressure generating means.

To summarise, an osmotic pump is described herein which uses a pressurized solvent to keep the osmotic pump close to its designated pump rate. Switching between different pump rates is possible by bypassing the semi-permeable membrane or by charging separate second chambers which are separated from the osmotic agent by a respective semi-permeable membrane. Pressure generating means including energy storage is used to pressurise the solvent in the or each second chamber and to optionally bypass the semi-permeable membrane.

The osmotic pump has many advantages. One advantage is that the osmotic pump can be stored ready to use for indefinite periods of time. A further advantage relates to its easy activation either by operation of a valve or when the reservoir 7 is filled with the solvent and the pressure device 60 pushes the solvent into second chamber 15. Delivery of a desired flow rate without a substantial delay after activation of the pump is also an advantage of the osmotic pump. Furthermore, the osmotic pump can be easily stopped at any time of operation by activating the respective valve. Accordingly, the osmotic pump can be stopped and restarted repeatedly during operation. Different selectable flow rates can be provided by the osmotic pump. Particularly, the osmotic pump as described herein can be arranged to provide bolus dosages of a fluid in addition to a basal flow rate. Moreover, the osmotic pump is capable to provide bolus dosages of well defined volumes. Furthermore, the osmotic pump can provide bolus dosages of fluid for pre-defined periods of time. According to a further aspect, the osmotic pump is capable of providing very high flow rates in respect to a basal flow rate of the osmotic pump in order to flush the fluidic pathway of a specific application. The osmotic pump can be activated automatically when fluidically connected to an application as described above. Furthermore, the osmotic pump can stop automatically when fluidically disconnected from the application. In addition to that, the osmotic pump may stop automatically when a pre-defined total volume is pumped out.

The osmotic pump can be used for medical applications, for example for drug delivery, sampling in organs and tissues or as a drive for fluids in analytical medical equipment, extra-corporeal medical applications on extracted organs and tissues and taken body fluids, and for non-medical applications such as microanalysis, microchromatography, microreaction technology, environmental analysis and power generation.

The written description above uses specific embodiments to disclose the invention, including the best mode, and also to enable any person skilled in the art to make and use the invention. While the invention has been described in terms of various specific embodiments, those skilled in the art will recognise that the invention can be practiced with modifications within the spirit and scope of the claims. Especially, mutually non-exclusive features of the embodiments described above may be combined with each other. The patentable scope is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

PARTS LIST

1 Housing of the pump
2 First cavity
3 Second cavity
4 Plunger/movable member
5 Movable impermeable barrier
6 Cavity for pressure generating means or energy storage/fourth chamber
7 Reservoir for solvent/third chamber
8 Reservoir for osmotic agent/first chamber
9 Reservoir for pumped fluid
10 Pumped fluid
11 Outlet for pumped fluid or driving fluid (if applicable)/orifice of first cavity 2
12 Filling port for solvent
13 Channel connecting reservoir 7 to Cavity 15
14 Semipermeable membrane
15, 15' Cavity for Solvent bordered by membrane 14 second chamber
16 Pressurized gas/fluid
17 Solvent
18 Osmotic agent (solution)/driving fluid
19 Solid osmotic agent
20 Bore
21 Bore
22 Spring
23 Valve
24 Channel portion connecting reservoir 7 to valve 23, 29
25 Channel portion connecting valve 23, 29 to cavity 15
26 Channel connecting cavity 15 to cavity 27
27 Cavity for gas to be vented
28 Venting membrane
29 Multi-port valve
30 Filling port
31 Flow resistor
32 Channel/bypass for direct conduction of reservoir 7 to reservoir 8
33 Syringe
34 Bore
35 Outlet valve
36 Bypass channel
37 Filling port
38 Movable impermeable barrier
39 Filling port
40 Housing for fluid pouch 42/third chamber
41 Cavity for driving fluid/compartment
42 Fluid pouch
43 Fluid outlet
44 Piston/Spool
45 Outlet port
46 Valve
47 Valve inlet
48 Valve port
49 Valve port
50 Volatile liquid
60 Pressure device
61 Control valve in bypass 36

The invention claimed is:

1. An osmotic pump, comprising:
a first chamber (8) comprising an osmotically active substance (18);
a second chamber (15) for a solvent (17);
a semi-permeable barrier (14) separating the first chamber (8) from the second chamber (15), the semi-permeable barrier (14) being impermeable to the osmotically active substance (18) and permeable to the solvent; and
a position-independent pressure device (60);
characterized in that the second chamber (15) is arranged to be filled with the solvent (17), and that the position-independent pressure device (60) is in fluid communication with the second chamber (15) and arranged for pressurizing the solvent (17) in the second chamber (15).

2. The osmotic pump of claim 1, wherein the pressure device (60) comprises an energy storage for providing energy to pressurize the solvent (17).

3. The osmotic pump of claim 2, wherein the energy storage is a pressure storage.

4. The osmotic pump of claim 2, wherein the energy storage comprises a movable member (4, 38) for acting on the solvent (17).

5. The osmotic pump of claim 1, wherein the pressure device (60) comprises a third chamber (7) in fluid communication with the second chamber (15), the third chamber (7) for filling with the solvent (17).

6. The osmotic pump of claim 5, wherein the pressure device (60) further comprises a fourth chamber (6) separated from the third chamber (7) by the movable member (4, 38).

7. The osmotic pump of claim 1, further comprising a valve (23, 29) comprising at least a first and a second port, the first port being in fluid communication with the pressure device (60) and the second port being in fluid communication with the second chamber (15).

8. The osmotic pump of claim 1, further comprising a valve (61, 46) comprising at least a first and a second port, the first port being in fluid communication with the first chamber (8) and the second port being in fluid communication with the second chamber (15), wherein the valve being arranged to provide a direct fluid communication between the first chamber (8) and the second chamber (15).

9. The osmotic pump of claim 7, wherein the valve (29) further comprising at least a third port which is in fluid communication with at least one of a bypass, a further second chamber (15') being separated from the first chamber (8) by a semi-permeable membrane (14), and a filling port (30) for filling solvent into the pressure device (60).

10. The osmotic pump of claim 1, wherein the second chamber (15, 15') at least partially borders to a gas-permeable barrier.

11. The osmotic pump of claim 1, further comprising a gas vent in fluid communication with the second chamber (15) wherein the gas vent is formed by the gas-permeable barrier (28).

12. An osmotic pump, comprising:
a first chamber (8) comprising an osmotically active substance (18);
a second chamber (15) arranged to be filled with a solvent (17);
a semi-permeable barrier (14) separating the first chamber (8) from the second chamber (15), the semi-permeable barrier (14) being impermeable to the osmotically active substance (18) and permeable to the solvent; and a position-independent pressure device (60) in fluid communication with the second chamber (15), the pressure device (60) being arranged for pressurizing the solvent (17) in the second chamber (15);
wherein a valve (23, 29) comprises at least a first and a second port, the first port being in fluid communication with the pressure device (60) and the second port being in fluid communication with the second chamber (15).

13. An osmotic pump, comprising:
a first chamber (8) comprising an osmotically active substance (18);
a second chamber (15) arranged to be filled with a solvent (17);
a semi-permeable barrier (14) separating the first chamber (8) from the second chamber (15), the semi-permeable barrier (14) being impermeable to the osmotically active substance (18) and permeable to the solvent; and
a position-independent pressure device (60) in fluid communication with the second chamber (15), the pressure device (60) being arranged for pressurizing the solvent (17) in the second chamber (15); and
a valve (61, 46) comprising at least a first and a second port, the first port being in fluid communication with the first chamber (8) and the second port being in fluid communication with the second chamber (15), wherein the valve being arranged to provide a direct fluid communication between the first chamber (8) and the second chamber (15).

14. A method for controlling the flow of a solvent in an osmotic pump comprising a first chamber (8) which comprises an osmotically active substance (18), a second chamber (15) which comprises the solvent, and a semi-permeable barrier (14) separating the first chamber (8) from the second chamber (15), the semi-permeable barrier (14) being impermeable to the osmotically active substance (18) and permeable to the solvent, wherein the solvent is imbibed through the semi-permeable barrier (14) by osmosis, comprising the step of substantially permanently pressurizing the solvent in the second chamber (15);
characterized in that the second chamber is arranged to be filled with the solvent (17) and that a position-independent pressure device (60) is in fluid communication with the second chamber (15).

15. The method of claim 14, further comprising the step of charging an energy storage for providing energy to pressurize the solvent.

16. The method of claim 15, wherein the step of charging comprises one of tensing a spring, compressing a fluid, filling the energy storage with a volatile liquid, and filling the energy storage with a swellable hydrogel.

17. A fluidic system, comprising:
an osmotic pump, comprising a first chamber (8) comprising an osmotically active substance (18), a second chamber (15) arranged to be filled with a solvent (17), a semi-permeable barrier (14) separating the first chamber (8) from the second chamber (15), the semi-permeable barrier (14) being impermeable to the osmotically active substance (18) and permeable to the solvent, and a position-independent pressure device (60) being arranged for pressurizing the solvent (17) in the second chamber (15); and
a fluidic device connected to the osmotic pump, the fluidic device requiring a minimum pressure for pumping a fluid through the fluidic device, wherein the pressure device of the osmotic pump is arranged to provide a pressure which is at least equal to or higher than the minimum pressure of the fluidic device.

* * * * *